United States Patent
Jia et al.

(10) Patent No.: US 10,251,550 B2
(45) Date of Patent: Apr. 9, 2019

(54) SYSTEMS AND METHODS FOR AUTOMATED SEGMENTATION OF RETINAL FLUID IN OPTICAL COHERENCE TOMOGRAPHY

(71) Applicant: OREGON HEALTH & SCIENCE UNIVERSITY, Portland, OR (US)

(72) Inventors: Yali Jia, Portland, OR (US); Jie Wang, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 4 days.

(21) Appl. No.: 15/458,889

(22) Filed: Mar. 14, 2017

(65) Prior Publication Data

US 2018/0263490 A1 Sep. 20, 2018
US 2019/0046030 A9 Feb. 14, 2019

Related U.S. Application Data

(60) Provisional application No. 62/310,415, filed on Mar. 18, 2016.

(51) Int. Cl.
*G06K 9/00* (2006.01)
*A61B 3/10* (2006.01)
(Continued)

(52) U.S. Cl.
CPC ............ *A61B 3/102* (2013.01); *A61B 3/0025* (2013.01); *A61B 3/1241* (2013.01); *G06K 9/6218* (2013.01); *G06T 5/002* (2013.01); *G06T 5/20* (2013.01); *G06T 7/0012* (2013.01); *G06T 7/11* (2017.01); *G06T 7/62* (2017.01); *G06T 11/003* (2013.01); *G06T 2207/10101* (2013.01);
(Continued)

(58) Field of Classification Search
CPC ........ A61B 5/0033; G06T 2207/10101; G06T 2211/404
See application file for complete search history.

(56) References Cited

U.S. PATENT DOCUMENTS

2011/0275931 A1* 11/2011 Debuc .................. A61B 3/102
600/425
2014/0073917 A1* 3/2014 Huang ................ A61B 5/0066
600/427

(Continued)

OTHER PUBLICATIONS

Liu et al. ("Automated choroidal neovascularization detection algorithm for optical coherence tomography angiography", 2015).*
(Continued)

*Primary Examiner* — Avinash Yentrapati
(74) *Attorney, Agent, or Firm* — Schwabe, Williamson & Wyatt, P.C.

(57) ABSTRACT

Disclosed herein are methods and systems for the identification and characterization of fluid accumulation in the retina using OCT imaging. The disclosed methods and systems are directed to the automated segmentation of retinal fluid using 2D or 3D structural OCT scan images. Approaches for visualization and quantification of both intraretinal and subretinal fluid are presented. Methods are also disclosed for using OCT angiography data to improve the quality of retinal fluid segmentation, and to provide combined visualization of fluid accumulation and retinal vasculature to inform clinical interpretation of results.

28 Claims, 12 Drawing Sheets

Pre-processing     Retinal fluid segmentation     Post-processing   Quantification

(51) Int. Cl.

| | | |
|---|---|---|
| A61B 3/00 | (2006.01) | |
| A61B 3/12 | (2006.01) | |
| G06T 7/00 | (2017.01) | |
| G06T 7/11 | (2017.01) | |
| G06T 7/62 | (2017.01) | |
| G06K 9/62 | (2006.01) | |
| G06T 5/20 | (2006.01) | |
| G06T 5/00 | (2006.01) | |
| G06T 11/00 | (2006.01) | |

(52) U.S. Cl.
CPC .............. *G06T 2207/20212* (2013.01); *G06T 2207/30041* (2013.01); *G06T 2211/404* (2013.01)

(56) References Cited

U.S. PATENT DOCUMENTS

| | | | | |
|---|---|---|---|---|
| 2016/0174830 | A1* | 6/2016 | Rubin | A61B 3/102 351/206 |
| 2016/0227999 | A1* | 8/2016 | An | A61B 3/1233 |
| 2017/0035286 | A1* | 2/2017 | Meyer | A61B 3/102 |
| 2017/0169565 | A1* | 6/2017 | Huang | A61B 3/0025 |

OTHER PUBLICATIONS

Wang et al. ("Automated volumetric segmentation of retinal fluid on optical coherence tomography" Mar. 2016.*

Wang, Jie, et al. "Automated volumetric segmentation of retinal fluid on optical coherence tomography." Biomedical optics express 7.4 (2016): 1577-1589.*

Fernandez, Delia Cabrera. "Delineating fluid-filled region boundaries in optical coherence tomography images of the retina." IEEE Trans. Med. Imaging 24.8 (2005): 929-945.*

Wilkins, Gary R., Odette M. Houghton, and Amy L. Oldenburg. "Automated segmentation of intraretinal cystoid fluid in optical coherence tomography." IEEE Transactions on Biomedical Engineering 59.4 (2012): 1109-1114.*

Quellec, Gwénolé, et al. "Three-dimensional analysis of retinal layer texture: identification of fluid-filled regions in SD-OCT of the macula." IEEE transactions on medical imaging 29.6 (2010): 1321-1330.*

Chen, Xinjian, et al. "Three-dimensional segmentation of fluid-associated abnormalities in retinal OCT: probability constrained graph-search-graph-cut." IEEE transactions on medical imaging 31.8 (2012): 1521-1531.*

* cited by examiner

SYSTEMS AND METHODS FOR AUTOMATED SEGMENTATION OF RETINAL FLUID IN OPTICAL COHERENCE TOMOGRAPHY

CROSS REFERENCE TO RELATED APPLICATION

The present application claims priority to U.S. Provisional Patent Application No. 62/310,415, titled "SYSTEMS AND METHODS FOR AUTOMATED SEGMENTATION OF RETINAL FLUID IN OPTICAL COHERENCE TOMOGRAPHY," filed Mar. 18, 2016, the disclosure of which is hereby incorporated by reference in its entirety.

ACKNOWLEDGEMENT OF GOVERNMENT SUPPORT

This invention was made with the support of the United States government under the terms of Grant Numbers R01 EY024544 and DP3 DK104397 awarded by the National Institutes of Health. The United States government has certain rights in this invention.

FIELD

Generally, the field involves methods of using optical coherence tomography (OCT) to characterize structural features of the retina. More specifically, the field involves automated methods of processing volumetric OCT scans to measure retinal fluid accumulation.

BACKGROUND

Diabetic retinopathy (DR) is a microvascular disease characterized by hyper-permeability, capillary occlusion, and neovascularization. These pathophysiologic changes can lead to macular edema and proliferative diabetic retinopathy, which are responsible for most of the vision loss associated with DR. Therefore early detection and monitoring of these complications is important in preventing permanent visual impairment.

Optical coherence tomography (OCT) is a noninvasive volumetric imaging technique that uses principles of interferometry to provide depth-resolved cross-sectional and three-dimensional (3D) imaging of biological tissues. OCT can provide millimeter level penetration into the target tissue and has micrometer-scale axial and lateral resolution, making it well-suited for the characterization of microstructural features. In clinical ophthalmology, OCT is commonly used to detect diabetic macular edema (DME), a condition wherein leakage of fluid from blood vessels causes fluid accumulation in the central part of the retina (the macula). Response to treatment for DME is typically assessed by mapping the total retinal thickness and/or retinal volume, and current OCT platforms provide specific functionality to measure these quantities. However, these structural indices are not always good indicators of disease status and progression, because they combine the contributions of both retinal tissue and accumulated retinal fluid into a single composite measurement. This is problematic because retinal thickness and volume are influenced not only by vascular permeability, but by numerous other factors including ischemic atrophy and fibrosis. Thus, while retinal thickness and volume may increase with vascular leakage, they can also decrease due to ischemic atrophy in the setting of DME. This multiplicity of influences confounds attempts to correlate retinal thickness and volume measurements with vascular permeability in DME and other related disease states.

As an alternative to thickness and volume measurements, a direct quantification of fluid volume within the retina, including intraretinal fluid (IRF) and subretinal fluid (SRF), would provide a more robust and accurate biomarker of disease activity. Indeed, the clinical relevance of IRF and SRF on OCT is well established. Resolution or stabilization of IRF and SRF has been used as a main indicator of disease activity in numerous studies of DME, neovascular aged-related macular degeneration (AMD), and retinal vein occlusion. In such studies, direct detection of retinal fluid has been performed qualitatively through visual inspection of sequential OCT cross sections but the process is laborious and prone to operator bias and error. Thus, an automated method that detects and quantifies retinal fluid volume is needed to make analysis of retinal fluid accumulation practical in clinical settings.

While a few state-of-the-art algorithms to provide fluid segmentation on clinical two dimensional (2D) OCT images with DME have been presented, there remains a need for a robust automated method. Despite its clear applicability, automated detection of volumetric retinal fluid has been a poorly explored area in OCT. No commercial system offers this function, leaving the identification of fluid space to subjective assessment or to time-intensive manual delineation. An active contour approach (i.e., a gradient vector flow snake model) has been applied to extract fluid regions in retinal structure of AMD patients, but the method is slow and requires substantial grader input, including initial boundary location estimation. An approach has also been described for automated segmentation of retinal fluid in cystoid macular edema using a Cirrus OCT system. This method applies an empirical thresholding cutoff on the contrast enhance images by bilateral filtering, but sparse details were presented on the assessment of the segmentation reliability. A fully automated algorithm based on a kernel regression classification method has been presented to identify fluid-filled region in real world spectral domain OCT images of eyes with severe DME. However, this algorithm did not distinguish between IRF and SRF, nor did it distinguish focal from diffuse retinal thickening. Moreover, all of the aforementioned algorithms were developed for 2D OCT images only, not three dimensional (3D) volumetric datasets. Volumetric approaches have been introduced which use prior information to classify the fluid associated abnormalities based on feature- and layer-specific properties in comparison with the normal appearance of macula, but these methods are unable to provide a clean measurement of fluid-filled space and are not suited to clinical use.

Thus, there remains a need for a fully automated segmentation method to identify and quantify fluid-filled regions of the retina and subretina in a 3D OCT dataset. Such a tool would significantly enhance the clinical management of macular diseases associated with hyper-permeability.

SUMMARY

The present disclosure is directed to methods and systems for the identification and quantification of fluid accumulation in the retina using OCT imaging. Specifically, the disclosure is directed to automated methods for segmentation and quantification of retinal fluid accumulation using 2D or 3D structural OCT scan images.

In an embodiment disclosed herein, a segmentation method based on a fuzzy level-set paradigm is demonstrated. The disclosed method involves three main operations: (1) delineation of the boundaries of the retinal layers and flattening of the dataset; (2) segmentation of the fluid space within the retinal layers using a fully automated and self-adaptive fuzzy level-set method; and (3) removal of segmentation artifacts based on morphological characteristics of the segmented boundaries and the presence of vascular shadowing.

An aspect of the disclosed fuzzy level-set segmentation method is that it incorporates a rigorous classification algorithm to facilitate automation of the segmentation process and improve segmentation accuracy. This classification scheme removes the need for user-guided initialization and parameter tuning that is characteristic of conventional level-set methods. This classification scheme is also critical in applying the method to real world clinical situations where a wide variability of image quality (e.g., intensity variation) and pathology exists.

In an embodiment described herein, segmentations are performed on OCT cross sections in three orthogonal directions (e.g., B-scan images ordered along the x- and y-axes and C-scan images ordered along the z-axis). Compared to previously reported methods using 2D images alone, the disclosed method makes full use of the volumetric information in the OCT dataset and thereby improves segmentation performance. In an embodiment, the three segmentations are combined into a single volumetric representation using a rule-based approach to reconcile the segmented boundaries produced by the three directional segmentations. For example, a voting process may be used to determine which boundary voxels from the three directional segmentations are retained in the final volumetric segmentation of the dataset. This procedure further increases the accuracy of detecting true fluid voxels by the disclosed method.

The quality of the final segmentation may be further improved by identifying and rejecting false-positive fluid voxels. In an embodiment, this identification may be based on morphological characteristics of the detected fluid volumes. In other embodiments, false positive voxels may be pruned from the segmented dataset based on the correspondence between structural OCT data and OCT angiography data (e.g., identification of vascular shadowing effects).

In an embodiment, the disclosed methods for retinal fluid segmentation may be applied to structural OCT scans obtained using an OCT angiography system. OCT angiography data from such a system scan may be used to improve the accuracy of the volumetric measurements as described above, and also to present the retinal fluid segmentation results simultaneously with blood flow data to aid in clinical interpretation. In an embodiment, such presentation may be in either a 2D en face projection format, a 2D cross sectional format, a 3D format, or combinations thereof, and may combine both structural and angiography data. An aspect of the disclosed method is that by registering the structural (fluid accumulation) and functional (blood flow) information into a single 3D volume and presenting results in the aforementioned formats, clinicians can intuitively evaluate pathological structures and microvascular dysfunction simultaneously.

In an embodiment the segmented retinal fluid can be partitioned into intraretinal fluid (IRF) and subretinal fluid (SRF) sets for separate quantification and presentation. Such a partitioning can further aid clinical interpretation OCT scan data.

Although the disclosed method was developed using an OCT angiography scan pattern from a commercial spectral domain OCT (Optovue RTV-ue XR Avanti), it will be understood by one skilled in the art that the method can be applied to datasets acquired using any OCT device that generates planar or volumetric scans with or without accompanying angiography data. In such systems, removal of vascular shadowing artifacts can be implemented using a rejection criterion not tied to OCT angiography data, for example, an approach based on pixel intensity standard deviation.

This Summary is provided to introduce a selection of concepts in a simplified form that are further described below in the Detailed Description. This Summary is not intended to identify key features or essential features of the disclosed subject matter, nor is it intended to be used to limit the scope of the disclosed subject matter. Furthermore, the disclosed subject matter is not limited to implementations that solve any or all disadvantages noted in any part of this disclosure.

DETAILED DESCRIPTION

Figure 1:
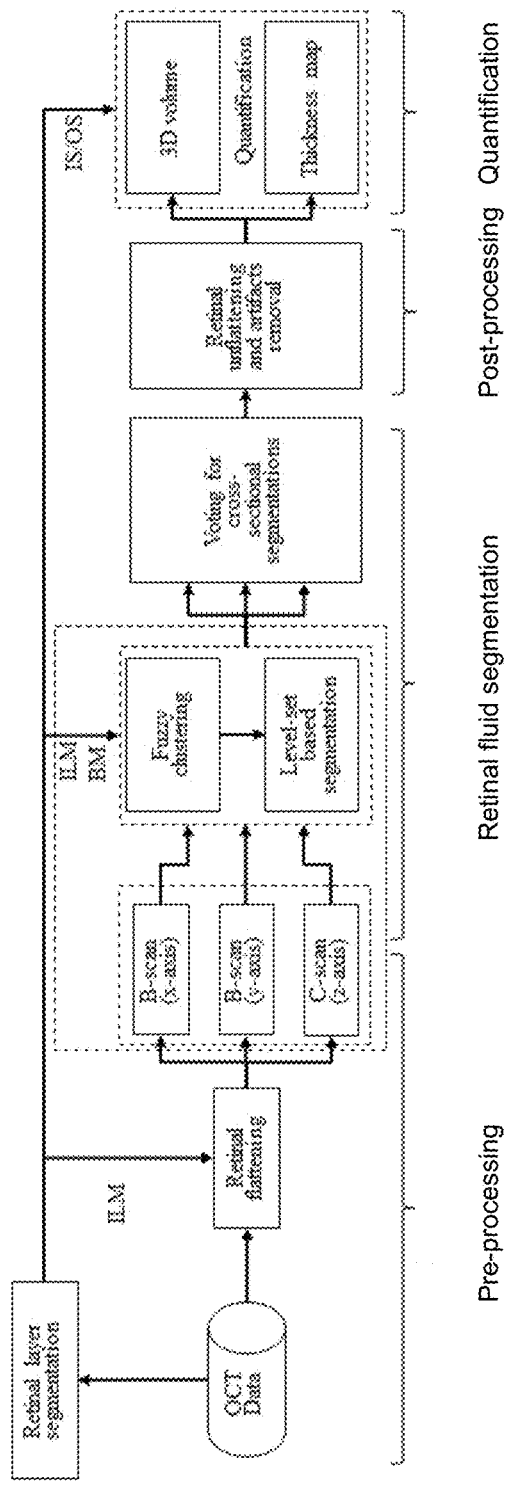
FIG. 1 shows an example of an automated volumetric retinal fluid detection algorithm. ILM: inner limiting membrane; BM: Bruch's membrane; IS/OS: junction of inner and outer photoreceptor segments.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging-based on the detection of spectral interference. Such imaging can be two-dimensional (2-D) or three-dimensional (3-D), depending on the application. Structural imaging can be of an extended depth range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is directed along the optical axis (the z-axis) of the OCT device and penetrates the sample being imaged. The A-scan encodes reflectivity information (for example, signal intensity) as a function of depth.

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image.

C-scan: A cross-sectional tomograph that can be achieved by combining a series of voxels at a given axial depth (i.e., z-direction) in a 3D OCT dataset. A C-scan encodes planar cross-sectional information from the sample and is typically presented as an image.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value or a decorrelation value). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A C-scan is made up of voxels at a specified depth (z-axis) in the data set; a B-scan can also be referred to as an image, and its constituent voxels referred to as pixels. A collection of adjacent B-scans or a collection of adjacent C-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset of decorrelation values reflecting flow within the imaged sample. There is a one-to-one correspondence between the voxels of the structural OCT dataset and the OCT angiography dataset. Thus, values from the datasets can be "overlaid" to present composite images of structure and flow (e.g., tissue microstructure and blood flow).

Optical coherence tomography (OCT) is an optical signal acquisition and processing method that is capable of capturing micrometer-resolution, two- and three-dimensional images from within optical scattering media, e.g., biological tissue. OCT is based on interferometric techniques and typically employs near-infrared light. The use of relatively long wavelength light allows it to penetrate into the scattering medium. As remarked above, among its many applications, OCT-based ocular imaging has found widespread clinical use and can be performed quickly and easily with minimal expertise. OCT is a non-invasive imaging modality which provides accurate and precise anatomical reproduction of the retinal layers thus is well suited for use in detecting and diagnosing diseases of the retina.

In recent years, OCT techniques have been extended to allow the detection of flow within scattering media, typically using speckle variance, decorrelation, phase-difference, or other approaches. Collectively these techniques are termed "OCT angiography" when applied to the detection of microcirculation within biological tissues. OCT angiography provides the ability to noninvasively map vasculature and microvascular beds within tissues. Applied to the retina, OCT angiography is well suited for visualizing and quantifying the integrity of retinal circulation pathways and for detecting abnormalities in ocular hemodynamics and vascular structure Disclosed herein is an automated volumetric segmentation method to detect and quantify retinal fluid in OCT datasets. In an embodiment described in greater detail below, a fuzzy level set method is used to identify the boundaries of fluid filled regions on B-scans (x and y-axes) and C-scans (z-axis). The boundaries identified from the B- and C-scans are combined to generate a comprehensive volumetric segmentation of retinal fluid. The volumetric segmentation is further refined to remove artefactual fluid regions by utilizing, for example, morphological characteristics of the segmented structures or by identifying vascular shadowing with OCT angiography obtained from the same scan.

Algorithm Overview

FIG. 1 illustrates an embodiment of the method for retinal fluid segmentation disclosed herein. A pre-processing operation is first performed to prepare the tissue region for segmentation. Fluid segmentation using fuzzy level-set method is then performed. Then, one or more post-processing operations may be applied to remove segmentation artifacts. The following three sections describe embodiments of each of these processes in detail.

(1) Pre-Processing

Figure 2:
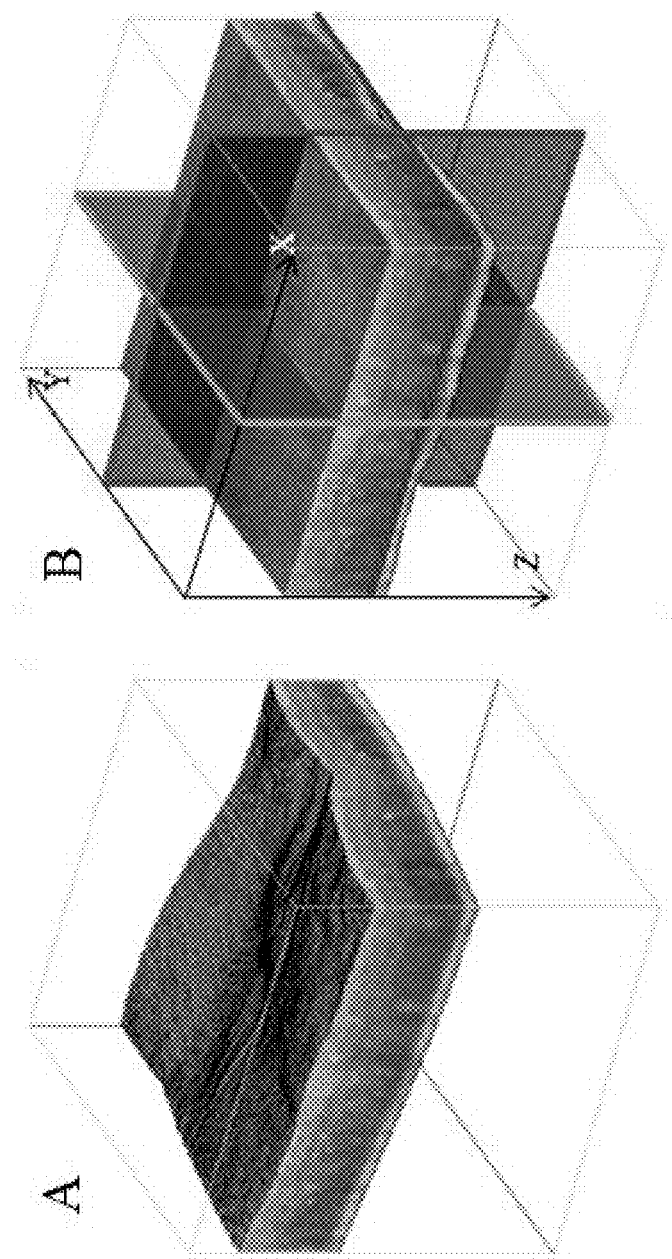
FIG. 2 shows an example of a flattening procedure used to segment retinal fluid as described herein. (A) Original OCT structural volume. (B) OCT structural volume flattened according to the inner limiting membrane (ILM) boundary. B-scans (x and y-axes) and C-scans (z-axis) are indicated as slices 202, 204, and 206, respectively.

The retina was defined as the region between inner limiting membrane (ILM) and Bruch's membrane (BM) as depicted in FIG. 2. Three dimensional structural OCT data (FIG. 2, panel A) was flattened using the ILM plane as a reference (FIG. 2, panel B). The junction of the inner and outer photoreceptor segments (IS/OS) defined the boundary between intraretinal fluid (IRF) and subretinal fluid (SRF). In an embodiment, these pre-processing steps can be performed using the methods described in M. Zhang, J. Wang, A. D. Pechauer, T. S. Hwang, S. S. Gao, L. Liu, L. Liu, S. T. Bailey, D. J. Wilson, and D. Huang, "Advanced image processing for optical coherence tomographic angiography of macular diseases," Biomedical optics express 6, 4661-4675 (2015), hereby incorporated by reference herein, or other suitable methods to delineate the surfaces separating specific retinal layers, and then flattening the three-dimensional data bounded by those surfaces relative to the ILM plane. Because of the tissue damage inherent to DME, automatic layer segmentation can fail even with robust algorithms.

Figure 3:
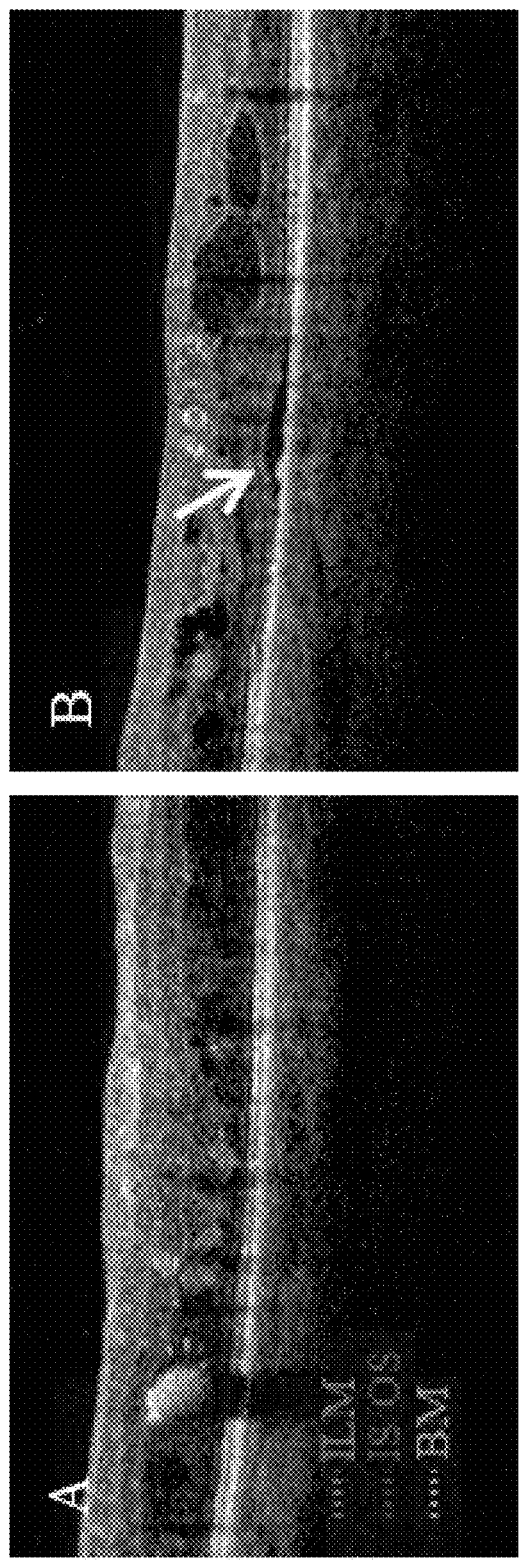
FIG. 3 shows an example of retinal layer boundaries segmented using the directional graph approach. (A) An example B-frame showing inner limiting membrane (ILM), Bruch's membrane (BM) and junction of inner and outer photoreceptor segments (IS/OS) boundaries may be automatically segmented. (B) An example B-frame with subretinal fluid showing IS/OS need be manually corrected in the position pointed by a white arrow.

FIG. 3 shows exemplary results from a graph search-based method for segmenting retinal layers. By using the graph search based segmentation method, ILM and BM can be automatically detected with a high degree of precision (FIG. 3, panel A), while IS/OS can require some manual intervention to correct errant segmentation results in datasets with SRF pathology (FIG. 3, panel B).

(2) Retinal Fluid Segmentation

In this stage, a fuzzy level-set method, specifically, a combination of fuzzy C-means (FCM) and a level set method, is implemented. Briefly, the intensity of retinal fluid is lower than that of retinal tissue, so fluid region can be clustered using FCM scored by probability. Then the boundary of the retinal fluid can be detected by a level-set method. A fuzzy level-set method is applied frame by frame on C-scans (along the z-axis) and B-scans (along the x- and y-axes) to identify fluid filled regions (FIG. 2, panel B). Three separate candidate volumetric segmentation results are obtained from these operations. These synthetic candidates are then combined into a single volumetric segmentation. In an implementation described below, a voting method is applied to the three volumetric segmentation results to classify each voxel as fluid or retinal tissue.

Fuzzy Level-Set Method

Level-set methods are widely used in image segmentation, and have recently been applied to detect abnormality in OCT 2D en face images. The level-set method represents the boundary of interest in image I as contour $\phi=0$ (i.e., the level-set curve), where the level-set function $\phi$, is a function of time and spatial coordinates in I. $\phi$ is initialized with an estimate of the segmentation and the level-set function evolves to produce the accurate boundary. In the method disclosed herein, the evolution of $\phi$ is implemented as follows:

$$\frac{\partial \phi}{\partial t} = \mu\left[\Delta\phi - div\left(\frac{\nabla\phi}{|\nabla\phi|}\right)\right] + \lambda\delta(\phi)div\left(g\frac{\nabla\phi}{|\nabla\phi|}\right) + g(1-2R_b)\delta(\phi) \quad (1)$$

where $\delta$ is the Dirac function, div is the divergence operator, and, $\mu$, $\lambda$, $R_b$ are estimated based the FCM result.

The first term on the right-hand side of the evolution equation (1) has two purposes: it smooths the level-set when $\phi$ is too steep ($|\Delta\phi|>1$) and makes the level-set steeper when $\phi$ is too smooth ($|\Delta\phi|<1$). The second and the third terms on the right-hand side of equation (1) are responsible for driving the zero level curves towards the boundary of interest.

Typically, a Gaussian smoothing operator is used to calculate the boundary weight g. However, because the dominant noise in OCT images is the speckle noise, a median operator M of the following form can be used instead:

$$g=1/[1+|\nabla M(I)|^2] \quad (2)$$

The median operator suppresses the noise while maintaining the edge sharpness in OCT images.

A drawback of the traditional level-set method is that its performance is subject to optimal configuration of the controlling parameters ($\mu$, $\lambda$ and $R_b$) and appropriate initialization of $\phi$ (e.g., an initial estimate of the segmentation). This initialization can require substantial manual intervention by the user. In contrast, the fuzzy level-set based method disclosed herein achieves full automation by first obtaining a probabilistic clustering result using the FCM. This clustering information is then used to determine the initialization and controlling parameters.

On OCT structural images, retinal fluid has a low intensity value compared to the high intensity of surrounding retinal tissue. Based on this intensity contrast, FCM assigns every pixel a probability of belonging to both the fluid and tissue cluster, by minimizing a cost function $$E = \sum_{i=1}^{K} \sum_{j=1}^{N} p_{i,j}^m \|I(j) - C(i)\|^2, \text{ with } \sum_{i}^{K} p_{i,j} = 1, \forall j = 1, 2, \ldots, N \quad (3)$$

where, K is a predetermined number of clusters, N is the number of pixels, $p_{i,j}$ is the probability of I(j) belong to the i-th cluster, and m is a initialized parameter (m>1) (in this study described herein, m=2). C(i) is the center of mass of the i-th cluster, and the C of the low intensity cluster is initialized using the mean intensity of vitreous region (above the ILM, top dark area in FIG. 3A). The $p_{i,j}$ and C(i) was updated by equation (4) during the iteration of the segmentation process using the following relationships:

$$\begin{cases} p_{i,j} = \left( \sum_{i=1}^{K} \left( \frac{\|I(j) - C(i)\|}{\|I(j) - C(k)\|} \right)^{2/(m-1)} \right)^{-1} \\ C(i) = \frac{\sum_{j=1}^{N} p_{i,j}^m I(j)}{\sum_{j=1}^{N} p_{i,j}^m} \end{cases} \quad (4)$$

Figure 4:
FIG. 4 shows an example of segmentation of an OCT structural B-scan using a fuzzy level set approach. (A) OCT structural B-scan (y-axis) image of a participant with severe macular edema. (B) Lowest intensity cluster generated by applying fuzzy C-means (FCM) on image (A). (C) Retinal fluid delineated by applying fuzzy level-set method on image (A).

FIG. 4 shows an example of segmentation of an OCT structural B-scan using the fuzzy level set approach. FIG. 4, panel A illustrates an OCT structural B-scan (y-axis) image of a participant with severe macular edema. The probability map $p_{i,j}$ of the lowest intensity cluster (FIG. 4, panel B) contains retinal fluid, vitreous, shadows of vessels, and other low intensity regions in or below retina. FCM results are used to initialize φ and calculate controlling parameters (μ, Δ, $R_b$ in equation (1)) for level-set evolution (detailed implementation can be found in B. N. Li, C. K. Chui, S. Chang, and S. H. Ong, "Integrating spatial fuzzy clustering with level set methods for automated medical image segmentation," Computers in Biology and Medicine 41, 1-10 (2011), incorporated by reference herein).

The fuzzy level-set based segmentation method disclosed herein is fully-automated and self-adaptive for images with quality variation. In the DME cases presented herein, the disclosed method was able to detect retinal fluid boundaries (shown in red on the B-scan (y-axis) FIG. 4, panel C) with few remaining artifacts. These remaining artifacts were filtered out according to the following operations.

Voting of Cross-Sectional Segmentations

Figure 5:
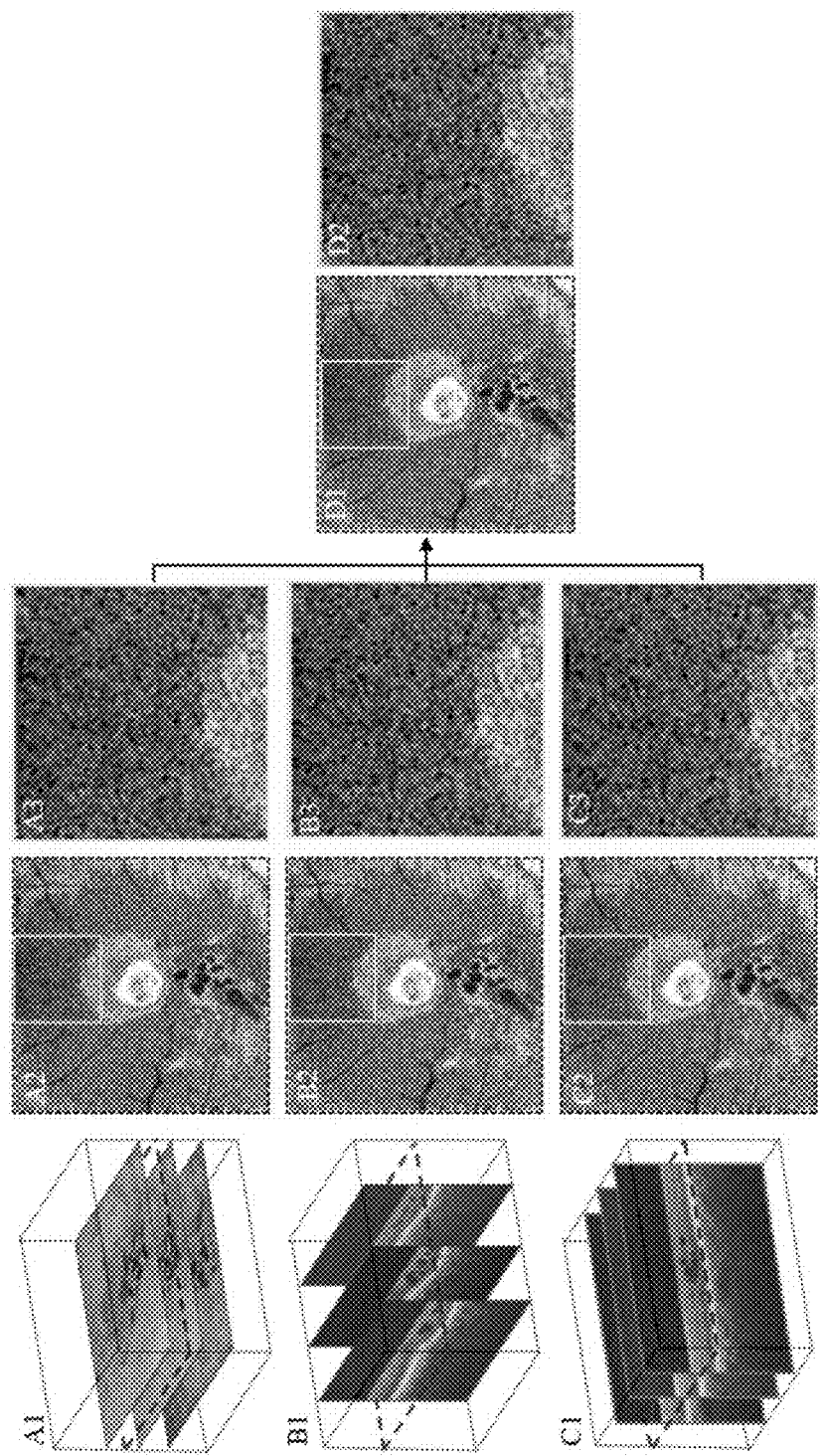
FIG. 5 shows an example of combining the segmentation results from three cross sectional orientations using a voting rule approach to improve the accuracy of retinal fluid segmentation. (A1), (B1) and (C1) are the segmentation results obtained by applying the fuzzy level-set method on C-scan and two B-scans, respectively. (A2), (B2) and (C2) are the segmentation results represented on a C-scan extracted from (A1), (B1) and (C1). (A3), (B3) and (C3) show a zoomed in perspective of the square region indicated in (A2), (B2) and (C2). (D1) is the segmentation result after voting. (D2) shows a zoomed-in perspective of the yellow square region in (D1). It can be seen that (D2) has much less error than (A3), (B3) and (C3).

Each voxel at location ω=(x, y, z) has a segmentation result for each of the three cross-sectional orientations ($S_{YZ}$, $S_{XZ}$ and $S_{YZ}$). These segmentations vary among the orientations due to differences in image contrast and bulk motion artifacts (FIG. 5 shows the segmentation regions, e.g., indicated by the boxes in panels A2, B2, and C2 that are shown in more detail in panels A3, B3, and C3, respectively). In order to improve segmentation accuracy, a voting rule may be used to automatically determine the segmentation results for each voxel. If a voxel is identified as belonging to retinal fluid in at least two of the cross-sectional orientations, it is considered to be "true" retinal fluid; otherwise, it is considered as retinal tissue. An example shown in FIG. 5 indicates the segmentation errors are dramatically reduced in the integrated results.

(3) Post-Processing

Voting of the results on three cross-sectional orientations improves the accuracy of segmentation. However, some segmentation artifacts still remain (e.g., FIG. 5, panel D1). For example, areas of retinal thickening or areas under vascular shadow have low intensity on OCT and can be misclassified as retinal fluid.

Figure 6:
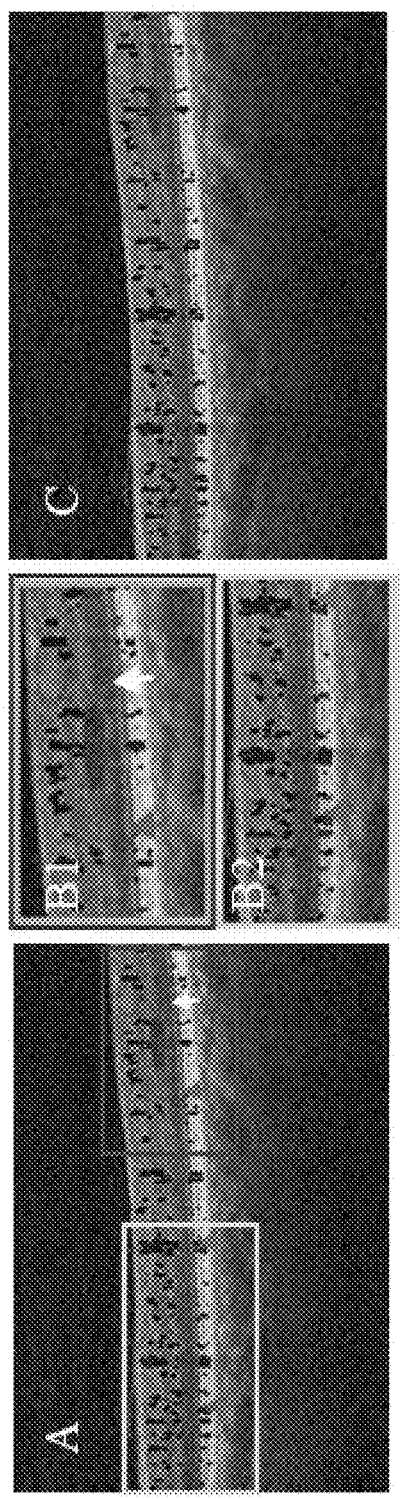
FIG. 6 shows an example of structural OCT B-scan images overlaid with split-spectrum amplitude-decorrelation algorithm (SSADA, marked as 602 in FIG. 6) and retinal fluid segmentation (marked as 604) results. (A) Before post-processing results where segmentation artifacts due to retinal thickening (arrow 606, arrows 608) and vascular shadow (arrow 610) can be seen in the square regions. (B1) and (B2) showed the zoomed in perspective of the square regions indicated in A. (C) After post-processing image where artifacts contained in the square regions have been removed.

Morphological characteristics can distinguish retinal thickening from retinal fluid. Generally, as depicted in FIG. 6, retinal fluid appears as a near-round region with smooth boundaries on OCT cross sections, while retinal thickening has boundaries that change sharply (FIG. 6, panels A and B1, marked with arrows 606). In an embodiment, the smoothness of the boundary quantified by both a shape descriptor and polar coordinates, in addition to the aspect ratio of the region, are all used to remove retinal thickening segmentation errors (FIG. 6, panels A, B1, and B2, marked with arrows 608).

Shape descriptors are reflected by the contour inflexion points of the detected regions. The contour C of the detected region can be expressed using two parametric functions x(l) and y(l): C=(x(l), y(l)). where l is a normalized parameter ranging from [0, 1], which represents the length variable. Curvature in variation levels were computed using equation (5).

$$\tau(l, \sigma_1) = \frac{X'(l, \sigma_1)Y''(l, \sigma_1) - Y'(l, \sigma_1)X''(l, \sigma_1)}{\{[X'(l, \sigma_1)]^2 + [Y'(l, \sigma_1)]^2\}^{3/2}} \quad (5)$$

where, X(l, $\sigma_1$) and Y(l, $\sigma_1$) are smoothed curves using Gaussian filter g(l, $\sigma_1$), X'(•) and X''(•) are first and second derivatives of length l, respectively, and Y'(•) and Y''(•) are first and second derivatives of length l, respectively. The zero-crossing of τ(l,$\sigma_1$) indicates the curvature inflexion.

Since the curve is expressed in polar coordinates, the curve variation can also be reflected in a one-dimensional sequence, following $$R(l, \sigma_2) = \left( \sqrt{[x(l) - X_o]^2 + [y(l) - Y_o]^2} \right) * g(l, \sigma_2) \quad (6)$$

where ($X_o$, $Y_o$) is the center of detected region. The inflexion of R(l,$\sigma_2$) is another parameter to evaluate smoothness.

In the study disclosed herein, $\sigma_1$=12, $\sigma_2$=6 were used in equations (5) and (6). Zero-crossings of τ(l,$\sigma_1$) and inflexions of R(l,$\sigma_2$) above the preset thresholds are identified as artifacts. Furthermore, the aspect ratio of the region, the ratio(r) between major axis and minor axis of the minimum enclosing ellipse, was also assessed.

Hemoglobin in perfused vessels absorbs and scatters the incident light of OCT and creates a vascular shadow. An OCT angiogram computed using the same OCT scan (for example, using the SSADA approach), can identify the locations of these blood vessels. By targeting the low intensity area associated with the vessels from the OCT angiogram, segmentation errors caused by vascular shadowing can be identified and removed. FIG. 6, panels A and B2 provide an example of the removal of the detected regions (indicated by arrow 610). This region can be differentiated as a segmentation error because the far left and far right points both fall within the vascular shadowing.

In the final step, the boundaries of volumetric detected regions are smoothed. In an embodiment, clutters with dimension smaller than 3 pixels on each axis are rejected. In such an embodiment applied to the examples disclosed herein, the smallest fluid volume that could be resolved would be 30×30×9.0 µm³.

EXAMPLES

The following examples are illustrative of the disclosed methods. In light of this disclosure, those skilled in the art will recognize that variations of these examples and other examples of the disclosed method would be possible without undue experimentation.

Example 1—Application to Diabetic Macular Edema

As described below, the accuracy of retinal fluid detection and quantification was evaluated on a set of eyes with diabetic macular edema. The disclosed automated segmentation method had good agreement with manually performed segmentation both qualitatively and quantitatively. In addition, the fluid map produced by the disclosed method can be integrated with OCT angiogram data for intuitive clinical evaluation.

Patient Selection and Data Acquisition

Participants diagnosed with DME with varied levels of retinopathy severity were recruited from the Casey Eye Institute. An informed consent was obtained and the protocol was approved by the Institutional Review Board at the Oregon Health & Science University. The study was conducted in compliance with the Declaration of Helsinki.

Two volumetric data sets were collected from single eyes of participants with DME within a visit. All of the data was acquired using a commercial spectral domain OCT system (RTVue-XR; Optovue, Fremont, Calif.) with a center wavelength 840 nm, a full-width half-maximum bandwidth of 45 nm, and an axial scan rate of 70 kHz. A single volumetric data set contained two volumetric raster scans covering a 3×3 mm area with a 2 mm depth. In the fast transverse scanning direction, 304 axial scans were sampled to obtain a single 3 mm B-scan. Two repeated B-scans were captured at a fixed position before proceeding to the next location. A total of 304 locations along a 3 mm distance in the slow transverse direction were sampled to form a 3D data cube. All 608 B-scans in each data cube were acquired in 2.9 seconds. Blood flow information was acquired using the split-spectrum amplitude-decorrelation (SSADA) between consecutive B-scans. For more detail on the SSADA technique, see S. S. Gao, G. Liu, D. Huang, and Y. Jia, "Optimization of the split-spectrum amplitude-decorrelation angiography algorithm on a spectral optical coherence tomography system," Optics letters 40, 2305-2308 (2015); and Y. Jia, O. Tan, J. Tokayer, B. Potsaid, Y. Wang, J. J. Liu, M. F. Kraus, H. Subhash, J. G. Fujimoto, and J. Hornegger, "Split-spectrum amplitude-decorrelation angiography with optical coherence tomography," Optics express 20, 4710-4725 (2012), both of which are incorporated by reference herein.

The SSADA algorithm detected blood flow by calculating the signal amplitude-decorrelation between consecutive B-scans. OCT structural images were obtained by averaging two repeated B-scans. The structural and angiography data were generated simultaneously on each scan. For each volumetric data set, two volumetric raster scans, including one x-fast scan and one y-fast scan were registered and merged through an orthogonal registration algorithm. The digital resolution is 10×10×3.0µm³/pixel.

One eye of sixteen DME participants was scanned. Ten eyes had retinal fluid in the macular scans based on clinician grading. These were used to test the automated algorithm.

Computer Implementation

The segmentation method depicted in FIG. 1 was implemented with custom software written in Matlab 2011a (Mathworks, Natick, Mass.) installed on a workstation with Intel(R) Xeon(R) CPU E3-1226 v3 @ 3.30 GHz and 16.0 GB RAM.

Quantification and Visualization

The fluid volumes were calculated as the product of the number of detected voxels and the voxels dimension (10× 10×3.0 µm) in each scan. Fluid thickness maps were generated by calculating the product of the number of detected voxels and voxel size in each axial position. This was then projected on 2D en face maps. Fluid voxels above the IS/OS reference plane were classified as IRF and those below as SRF. This allowed separate volume calculations and thickness maps of IRF and SRF to be made.

Three-dimensional renderings of retinal fluid were constructed using the 3D visualization module of ImageJ. These 3D renderings of retinal fluid can be combined with OCT angiography (e.g., en face angiograms) to visualize the retinal fluid in relation to vasculature (see, for example, FIG. 9, panel F). In the example presented here, the en face OCT angiogram was created by projecting the maximum SSADA flow signals internal to BM boundary.

Verification of Results

To evaluate the accuracy of the proposed method, automatic segmentation results were compared with manually corrected segmentation results which served as a "ground truth" reference. An expert human grader manually corrected the boundaries detected by automated algorithm through the entire volumetric data set. The correction was done on the OCT orientation with the clearest fluid boundaries for contouring. During correction, the grader compared the structural OCT frames at all three orientations to make a grading decision, and used an editing tool incorporated in the same software interface to delineate the correct fluid boundary. The smallest fluid region that the editing tool could resolve was 9 pixels. In order not to introduce too much error during contouring, the regions smaller than this were neglected.

The Jaccard similarity metric (J) was used for comparison, which is defined as $$J = \frac{|S \cap G|}{|S \cup G|} \quad (7)$$

where S is the automated segmentation results, G is the ground truth (i.e., the manually corrected results based on S). The Jaccard coefficient ranges from 0 to 1, where 1 denotes the two were identical and 0 if they were completely different. Errors rates were also computed by comparison to ground truth. False positive error was the ratio of the total number of automatically segmented pixels that were not included in the manual segmentation result to the total number of ground truth pixels. False negative error was the ratio of the total number of manually segmented pixels that were not included in the automated segmentation result to the total number of ground truth pixels. The difference between the automated segmentation results and ground truth is described as the total number of false positive and false negative errors.

Intra-visit repeatability of the proposed method was assessed using intra-class correlation (ICC).

Results

Figure 7:
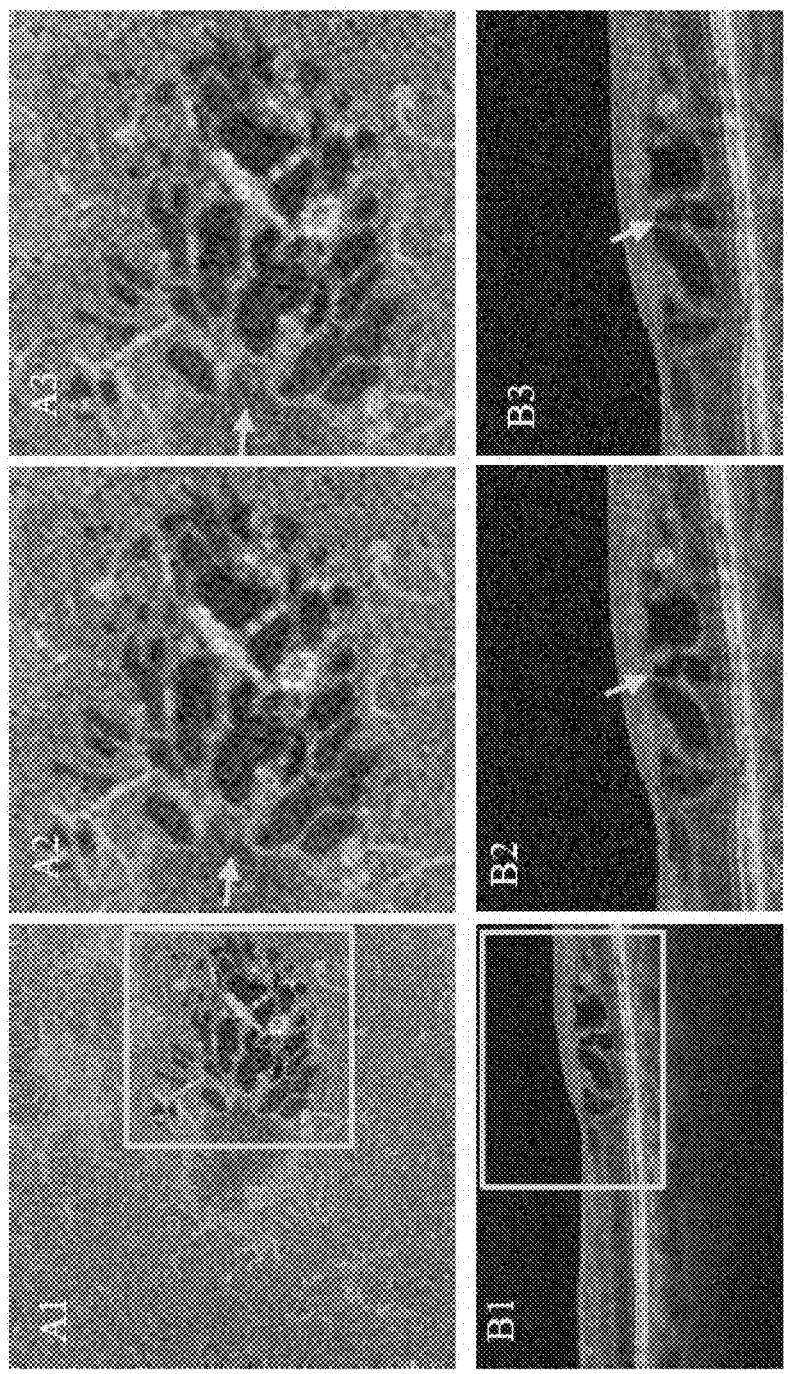
FIG. 7 shows an example of segmentation results obtained using the disclosed methods compared to manual delineation performed by a human expert. (A1) and (B1) are original images on C-scan and B-scan. (A2) and (B2) are segmentation results of the proposed method. (A3) and (B3) are ground truth delineated by human expert. Arrows identify the false positive segmentation results corrected by an expert human grader.
Figure 8:
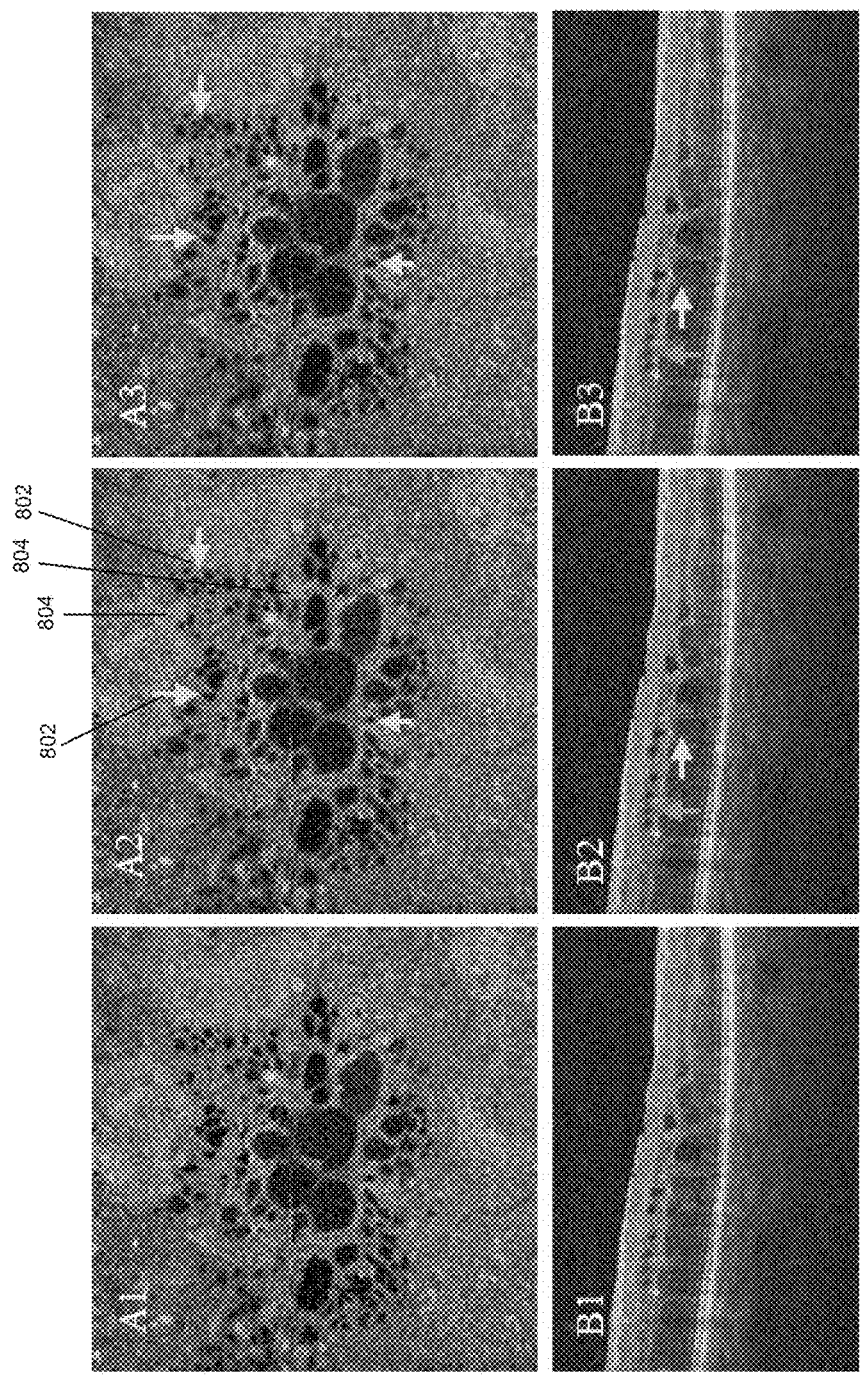
FIG. 8 shows an example of segmentation results obtained using the disclosed methods compared to manual delineation performed by a human expert in a case with both IRF and SRF. (A1) and (B1) are original images on C-scan and B-scan. (A2) and (B2) are segmentation results of the disclosed method. (A3) and (B3) are ground truth delineated by a human expert. Arrows 802 identify the false negative segmentation results corrected by an expert human grader. Arrows 804 identify the rejected regions by both automated algorithm and manual correction.

The results from automated fuzzy level-set algorithm were compared with the results from manual correction (ground truth). Data from a single eye of 10 participants with DME were analyzed. The results from two representative cases are shown in FIG. 7 and FIG. 8. The first case (FIG. 7) has IRF only and showed high image contrast between IRF and surrounding tissues. The second case (FIG. 8) had both IRF and SRF, where contrast was low between retinal fluid and tissue. The second case also exhibited diffuse retinal thickening. The fuzzy level-set algorithm automatically outlined the boundary of fluid space. The algorithm required about 26 minutes of processing time on an Intel Xeon CPU (E3-1226, 3.3 GHz), of which 73% of the time was spent on the iteration of fuzzy level-set segmentation. Segmentation of each orientation required 6 minutes of processing time.

A qualitative comparison between both B-scans and C-scans showed a very small difference between the fuzzy level-set algorithm and expert grading. This difference was due to false positive segmentation where the boundaries between intraretinal fluid spaces are indistinct (FIG. 7, panel B2) and due to the retinal thickening causing extremely low intensity (FIG. 7, panel A2). Some difference was due to false negative segmentation (FIG. 8, panel A2 and FIG. 8, panel B2) where the real fluid detected region can be excluded in the step of removing clutters during post-processing. Fluid regions appearing as black holes on C-scans were infrequently missed by the manual grading. This is due to the indistinct size and boundary of small fluid regions (indicated by arrows 804 in FIG. 8).

Figure 9:
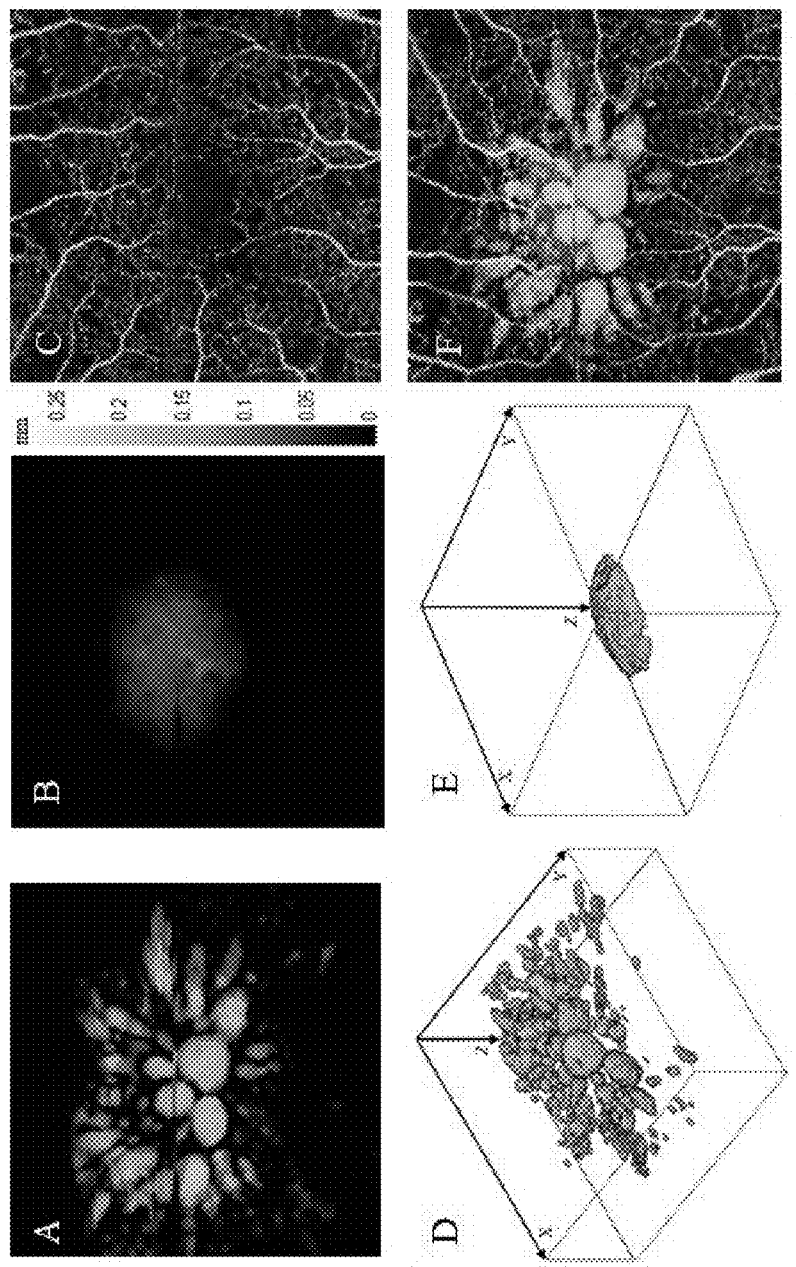
FIG. 9 shows an example of quantification of volumetric spaces of retinal fluid using the disclosed methods. (A) Thickness maps of intraretinal fluid (IRF). (B) Thickness maps of subretinal fluid (SRF). (C) En face retinal OCT angiogram. (D) 3D rendering of IRF volume. (E) 3D rending of SRF volume. (F) OCT angiogram overlaid with retinal fluid thickness map.

Quantitatively, the fuzzy level-set algorithm agreed well with manual grading (Table 1 and Table 2). Repeatability of retinal fluid measurement was computed from the 2 sets of OCT scans obtained from each eye. The automated method had excellent repeatability as measured by an ICC value of 0.976.

volumetric fluid spaces were rendered separately (FIG. 9, panels D and E). The detected IRF in the case shown in FIG. 9, panels A and D appears as a petaloid pattern with fluid spaces clumped in close proximity. The detected SRF of FIG. 9, panels B and E appear as a large contiguous dome shape, consistent with the morphology seen in the classical pattern. An en face composite map combining a fluid volume map and an en face angiogram presents the vasculature and the fluid cysts in an intuitive fashion and highlights the relationship between the vascular and anatomic changes in DR (FIG. 9, panels C and F).

Example 2—OCT Image Processing System

Figure 10:
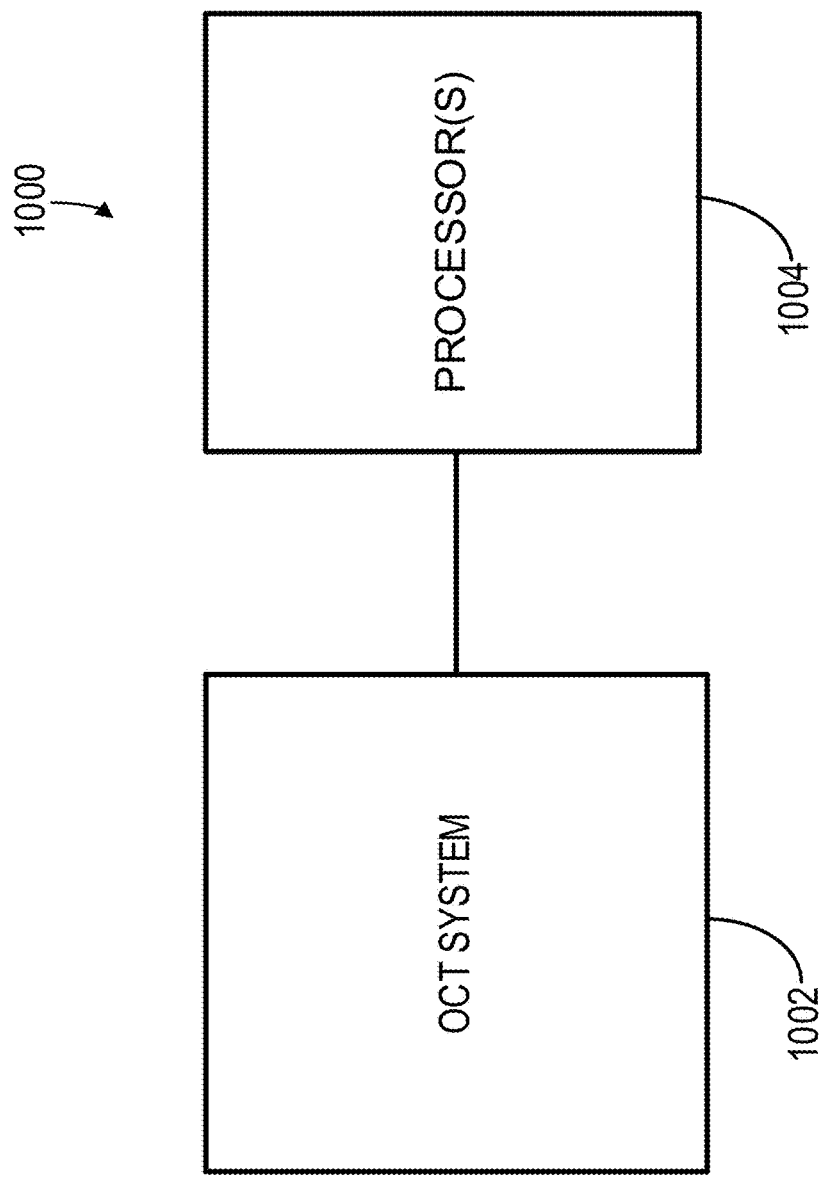
FIG. 10 schematically shows an example system processing OCT datasets to suppress shadowgraphic flow projections in OCT angiography datasets in accordance with the disclosure.

FIG. 10 schematically shows an example system 1000 for OCT image processing in accordance with various embodiments. System 1000 comprises an OCT system 1002 configured to acquire an OCT image comprising OCT interferograms and one or more processors or computing systems 1004 that are configured to implement the various processing routines described herein. OCT system 1000 can comprise an OCT system suitable for OCT angiography applications, e.g., a swept source OCT system. For example, the OCT system 1002 may include all or selected aspects of the system 1200 shown in FIG. 12. In some embodiments, the processor(s) 1004 shown in FIG. 10 may correspond to the computer 1220 shown in FIG. 12.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors.

TABLE 1

The retinal fluid volumes detected by automated algorithm and ground truth

| | | Case | | | | | | | | | |
|---|---|---|---|---|---|---|---|---|---|---|---|
| | | 1 | 2 | 3 | 4 | 5 | 6 | 7 | 8 | 9 | 10 |
| Fluid volume ($mm^3$) | Ground truth | 0.286 | 0.290 | 0.051 | 0.022 | 0.020 | 0.027 | 0.059 | 0.232 | 0.139 | 0.052 |
| | Fuzzy level-set | 0.297 | 0.336 | 0.048 | 0.024 | 0.019 | 0.020 | 0.065 | 0.246 | 0.132 | 0.051 |
| | Difference | 0.037 | 0.068 | 0.009 | 0.005 | 0.005 | 0.007 | 0.021 | 0.044 | 0.023 | 0.006 |

TABLE 2

Agreement between automated algorithm and ground truth

| | |
|---|---|
| Jaccard similarity metric | 0.811 ± 0.052 |
| False positive error | 0.092 ± 0.036 |
| False negative error | 0.121 ± 0.061 |

FIG. 9 shows exemplary visualizations of the segmented retinal fluid spaces. To better visualize the segmented fluid spaces, the thicknesses of IRF and SRF were projected separately on 2D map (FIG. 9, panels A and B), and 3D In various embodiments, data and/or information can be displayed, and an operator can input information in response thereto.

In some embodiments, the above described methods and processes can be tied to a computing system, including one or more computers. In particular, the methods and processes described herein, e.g., the method depicted in FIG. 1 described above, can be implemented as a computer application, computer service, computer API, computer library, and/or other computer program product.

Figure 11:
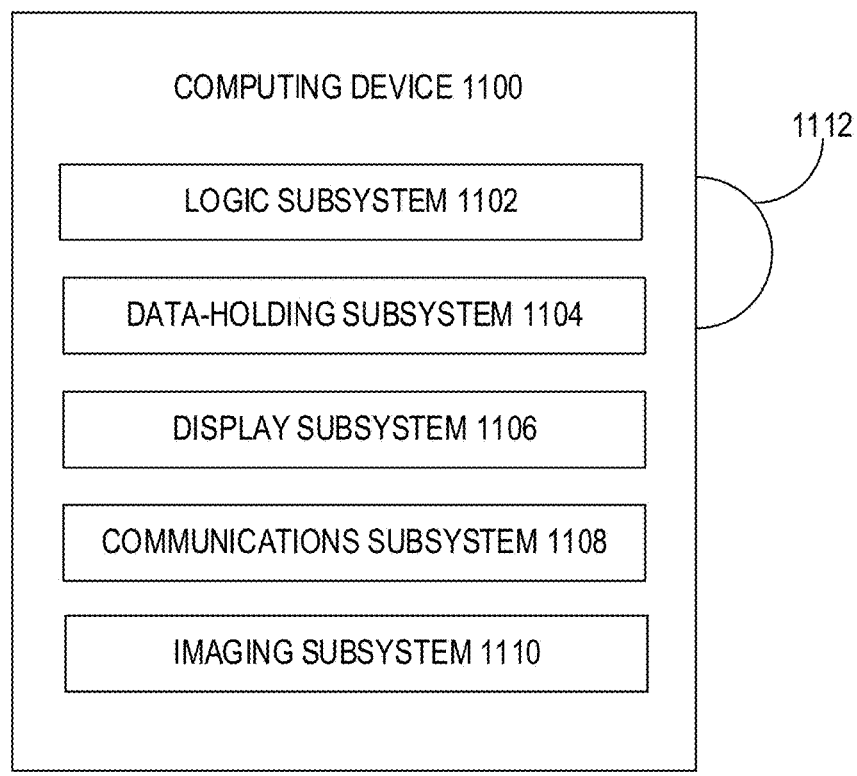
FIG. 11 schematically shows an example of a computing system in accordance with the disclosure.

FIG. 11 schematically shows a non-limiting computing device 1100 that can perform one or more of the above described methods and processes. For example, computing device 1100 can represent a processor included in system 1000 described above, and can be operatively coupled to, in communication with, or included in an OCT system or OCT image acquisition apparatus. Computing device 1100 is shown in simplified form. It is to be understood that virtually any computer architecture can be used without departing from the scope of this disclosure. In different embodiments, computing device 1100 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1100 includes a logic subsystem 1102 and a data-holding subsystem 1104. Computing device 1100 can optionally include a display subsystem 1106, a communication subsystem 1108, an imaging subsystem 1110, and/or other components not shown in FIG. 11. Computing device 1100 can also optionally include user input devices such as manually actuated buttons, switches, keyboards, mice, game controllers, cameras, microphones, and/or touch screens, for example.

Logic subsystem 1102 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 1104 can include one or more physical, non-transitory, devices configured to hold data and/or instructions executable by the logic subsystem to implement the herein described methods and processes. When such methods and processes are implemented, the state of data-holding subsystem 1104 can be transformed (e.g., to hold different data).

Data-holding subsystem 1104 can include removable media and/or built-in devices. Data-holding subsystem 1104 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1104 can include devices with one or more of the following characteristics: volatile, nonvolatile, dynamic, static, read/write, read-only, random access, sequential access, location addressable, file addressable, and content addressable. In some embodiments, logic subsystem 1102 and data-holding subsystem 1104 can be integrated into one or more common devices, such as an application specific integrated circuit or a system on a chip.

FIG. 11 also shows an aspect of the data-holding subsystem in the form of removable computer-readable storage media 1112, which can be used to store and/or transfer data and/or instructions executable to implement the herein described methods and processes. Removable computer-readable storage media 1112 can take the form of CDs, DVDs, HD-DVDs, Blu-Ray Discs, EEPROMs, flash memory cards, USB storage devices, and/or floppy disks, among others.

When included, display subsystem 1106 can be used to present a visual representation of data held by data-holding subsystem 1104. As the herein described methods and processes change the data held by the data-holding subsystem, and thus transform the state of the data-holding subsystem, the state of display subsystem 1106 can likewise be transformed to visually represent changes in the underlying data. Display subsystem 1106 can include one or more display devices utilizing virtually any type of technology. Such display devices can be combined with logic subsystem 1102 and/or data-holding subsystem 1104 in a shared enclosure, or such display devices can be peripheral display devices.

When included, communication subsystem 1108 can be configured to communicatively couple computing device 1100 with one or more other computing devices. Communication subsystem 1108 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 1100 to send and/or receive messages to and/or from other devices via a network such as the Internet.

When included, imaging subsystem 1110 can be used acquire and/or process any suitable image data from various sensors or imaging devices in communication with computing device 1100. For example, imaging subsystem 1110 can be configured to acquire OCT image data, e.g., interferograms, as part of an OCT system, e.g., OCT system 1002 described above. Imaging subsystem 1110 can be combined with logic subsystem 1102 and/or data-holding subsystem 1104 in a shared enclosure, or such imaging subsystems can comprise periphery imaging devices. Data received from the imaging subsystem can be held by data-holding subsystem 1104 and/or removable computer-readable storage media 1112, for example.

Figure 12:
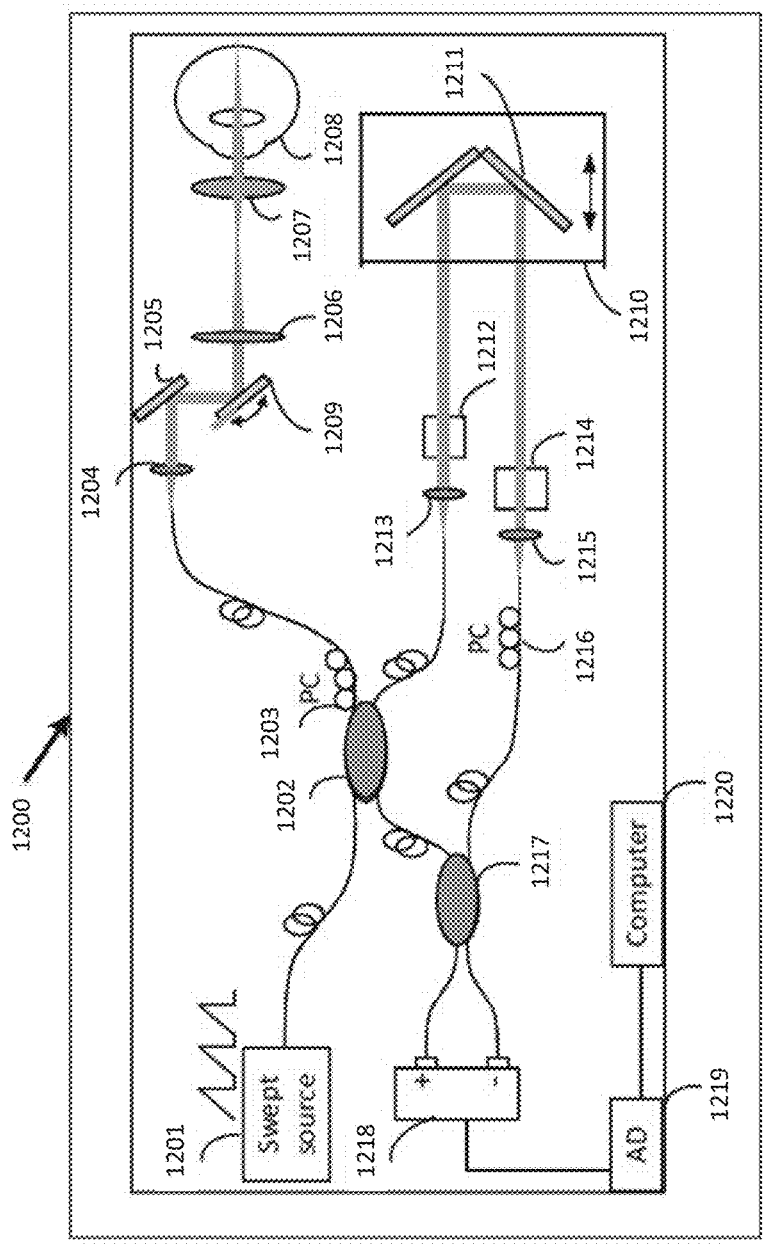
FIG. 12 schematically shows an OCT system that may be used to practice various embodiments disclosed herein.

FIG. 12 schematically illustrates an in vivo imaging system 1200 for collecting OCT image information. In some embodiments, the system 1200 may correspond to the system 1000 shown in FIG. 10 and/or the system 1100 shown in FIG. 11. For example, the computer 1220 may correspond to the one or more processors 1004, and some or all of the remaining components of system 1200 may correspond to the OCT system 1002 of FIG. 10.

The system 1200 may be, for example, a high-speed swept-source OCT system 1200 (e.g., as described in B. Potsaid, B. Baumann, D. Huang, S. Barry, A. E. Cable, J. S. Schuman, J. S. Duker, and J. G. Fujimoto, "Ultrahigh speed 1050 nm swept source/fourier domain oct retinal and anterior segment imaging at 100,000 to 400,000 axial scans per second," Opt. Express 18(19), 20029-20048 (2010)) can used to demonstrate the methods described herein. High speed swept-source OCT system 1200 comprises a tunable laser 1201. For example, tunable laser 1201 (e.g., a tunable laser from Axsun Technologies, Inc, Billerica, Mass., USA) may have a wavelength of 1050 nm with 100 nm tuning range, a tuning cycle with a repetition rate of 100 kHz and a duty cycle of 50%. Such OCT system 1200 can produce a measured axial resolution of 5.3 μm (full-width-half-maximum amplitude profile) and an imaging range of 2.9 mm in tissue. Light from swept source 1201 can be coupled into a two by two fiber coupler 1202 through single mode optical fiber. One portion of the light (e.g., 70%) can proceed to the sample arm (i.e., the patient interface), and the other portion of the light (e.g., 30%) can proceed to the reference arm.

In the sample arm, a sample arm polarization control unit 1203 can be used to adjust light polarization state. The exit light from the fiber coupler 1202 can then be coupled with a retinal scanner whereby the light is collimated by sample arm collimating lens 1204 and reflected by mirror 1205 and two dimensional galvo scanner 1209 (e.g., an XY galvonanometer scanner). Two lenses, first lens 1206 (e.g., an objective lens) and second lens 1207 (e.g., an ocular lens) can relay probe beam reflected by galvo scanner 1209 into a human eye 1208. For example, a focused spot diameter of 18 μm (full-width-half-maximum amplitude profile) can be calculated on the retinal plane based on an eye model. The average light power (i.e., output power of the laser) onto a human eye can be 1.9 mW, which is consistent with safe ocular exposure limit set by the American National Standard Institute (ANSI).

The reference arm can comprise a first reference arm collimating lens 1213, a water cell 1212, a retro-reflector 1211, a glass plate 1214 and a second reference arm collimating lens 1215. Glass plate 1214 can be used to balance the dispersion between the OCT sample arm and reference arm. Water cell 1212 can be used to compensate the influence of dispersion in the human eye 1208. Retro-reflector 1211 can be mounted on a translation stage 1210 which can be moved to adjust the path length in the reference arm.

Light from the sample and reference arm can interfere at beam splitter 1217. A reference arm polarization control unit 1216 can be used to adjust the beam polarization state in the reference arm to maximum interference signal. The optical interference signal from beam splitter 1217 (e.g., a 50/50 coupler) can be detected by a balanced detector 1218 (e.g., a balanced receiver manufactured by Thorlabs, Inc, Newton, N.J., USA), sampled by an analog digital conversion unit 1219 (e.g., a high speed digitizer manufactured by Innovative Integration, Inc.) and transferred into computer 1220 for processing. For example, computer 1220 can be used for storing instructions for, and implementing, the methods described herein. Interference fringes, for example, can be recorded by analog digital conversion unit 1219 at 400 MHz with 14-bit resolution, with the acquisition driven by the optical clock output of tunable laser 1201. In such an exemplary setup, imaging system 1200, sensitivity can be measured with a mirror and neutral density filter at 95 dB, with a sensitivity roll-off of 4.2 dB/mm.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method of quantifying retinal fluid volume in an optical coherence tomography (OCT) dataset, comprising:
   obtaining a structural OCT dataset, wherein the structural OCT dataset is comprised of B-scan images and C-scan images;
   delineating a first retina layer boundary from the structural OCT dataset;
   delineating a second retina layer boundary from the structural OCT dataset;
   segmenting the B-scan images and the C-scan images in a region between the first retina layer boundary and the second retina layer boundary to obtain a 3D retinal fluid segmentation; and
   calculating a volume of fluid enclosed by the 3D retinal fluid segmentation.

2. The method of claim 1, further comprising flattening, prior to segmenting the B-scan images and the C-scan images, the structural OCT dataset using the first retina layer boundary as a reference plane, thereby generating a flattened structural OCT dataset, wherein the segmenting the B-scan images and the C-scan images includes segmenting the B-scan images and the C-scan images of the flattened structural OCT dataset.

3. The method of claim 2, wherein the segmenting the B-scan images and the C-scan images includes:
   segmenting the B-scan images of the flattened structural OCT dataset in an x-direction, the segmenting limited to the region between the first retina layer boundary and second retina layer boundary, thereby generating an x-direction segmentation;
   segmenting the B-scan images of the flattened structural OCT dataset in a y-direction, the segmenting limited to the region between the first retina layer boundary and second retina layer boundary, thereby generating an y-direction segmentation;
   segmenting the C-scan images of the flattened structural OCT dataset in the z-direction, wherein the segmenting is limited to the region between the first retina layer boundary and second retina layer boundary, thereby generating a z-direction segmentation; and
   combining the x-direction segmentation, y-direction segmentation, and z-direction segmentation, thereby generating the 3D retinal fluid segmentation.

4. The method of claim 3, wherein segmenting the B-scan or C-scan images comprises:
   selecting a B-scan or C-scan image from the structural OCT dataset;
   calculating a clustering probability map for the B-scan or C-scan image;
   calculating a set of parameter values based on the clustering probability map;
   initializing a level set algorithm with the set of parameter values;
   applying the level set algorithm to the B-scan or C-scan image; and
   returning a segmented B-scan or C-scan image, wherein the boundaries of fluid-filled regions of the retina are delineated in the segmented B-scan or C-scan image.

5. The method of claim 4, wherein the clustering probability map is calculated using a fuzzy C-means algorithm.

6. The method of claim 3, wherein the combining the segmentations is performed using a voting method.

7. The method of claim 1, further comprising removing segmentation artifacts from the 3D retinal fluid segmentation prior to calculating the volume of fluid enclosed by the 3D retinal fluid segmentation.

8. The method of claim 7, wherein the removing segmentation artifacts from the 3D retinal fluid segmentation comprises:
   selecting a segmented B-scan image;
   selecting a segmentation contour within the segmented B-scan image;
   applying a Gaussian filter to the segmentation contour, thereby generating a smoothed contour;
   calculating a curvature equation for the smoothed contour according to:

$$\tau(l, \sigma_1) = \frac{X'(l, \sigma_1)Y''(l, \sigma_1) - Y'(l, \sigma_1)X''(l, \sigma_1)}{\{[X'(l, \sigma_1)]^2 + [Y'(l, \sigma_1)]^2\}^{3/2}} \quad (5)$$

where, $X(l, \sigma_1)$ and $Y(l, \sigma_1)$ are smoothed curves using Gaussian filter $g(l, \sigma_1)$, $X'(\bullet)$ and $X''(\bullet)$ are first and second derivatives of length l, respectively, $Y'(\bullet)$ and $Y''(\bullet)$ are first and second derivatives of length l, respectively, and a zero-crossing of $\tau(l,\sigma_1)$ indicates a curvature inflexion;
   finding a first number of inflection points along the curvature equation; and
   removing the segmentation contour, provided that the first number of inflection points exceeds a first threshold value.

9. The method of claim 8, further comprising:
   calculating a polar coordinate equation for the smoothed contour according to:

$$R(l, \sigma_2) = \left(\sqrt{[x(l) - X_o]^2 + [y(l) - Y_o]^2}\right) * g(l, \sigma_2) \quad (6)$$

where $(X_o, Y_o)$ is a center of a detected region;
   finding a second number of inflection points along the polar coordinate equation; and
   removing the segmentation contour, provided that the second number of inflection points exceeds a second threshold value.

10. The method of claim 8, further comprising:
    calculating an aspect ratio for the smoothed contour, wherein the aspect ratio is determined from major and minor axes of a minimum ellipse enclosing the smoothed contour; and
    removing the segmentation contour, provided that the aspect ratio exceeds a third threshold value.

11. The method of claim 8, further comprising:
    obtaining an OCT angiography dataset, wherein the OCT angiography dataset is computed from the structural OCT dataset;
    selecting an angiography B-scan image from the OCT angiography dataset;
    identifying a vascular shadow in the angiography B-scan image; and
    removing the segmentation contour, provided that the segmentation contour is associated with a vascular shadow.

12. The method of claim 1, further comprising:
    smoothing the 3D retinal fluid segmentation, thereby generating a smoothed 3D retinal fluid segmentation;
    selecting a segmented volume within the smoothed 3D retinal fluid segmentation; and
    removing the segmented volume, provided that the size of the segmented volume along each axis is less than a size threshold value.

13. The method of claim 12, wherein the size threshold value is 3 pixels.

14. The method of claim 1, further comprising:
    obtaining an OCT angiography dataset, wherein the OCT angiography dataset is computed from the structural OCT dataset and comprised of voxels having a specified voxel dimension;
    classifying voxels in the 3D retinal fluid segmentation that are located inside a segmentation contour as fluid, thereby generating a set of fluid voxels;
    counting the fluid voxels along each axial position in the 3D retinal fluid segmentation, provided that the voxels are located between the first retina layer boundary and second retina layer boundary, thereby generating a set of fluid thickness counts;
    multiplying the fluid thickness counts by a voxel dimension, thereby generating a set of fluid thickness values; and
    generating a 2D fluid thickness map from the set of fluid thickness values.

15. The method of claim 14, further comprising:
    generating a 2D en face angiogram from the OCT angiography dataset, wherein the 2D en face angiogram image is generated using voxels located between the first retina layer boundary and second retina layer boundary;
    overlaying the 2D fluid thickness map on the 2D en face angiogram, thereby generating a combined thickness map and angiogram; and
    presenting the combined thickness map and angiogram.

16. The method of claim 14, further comprising:
    delineating a separating retina layer boundary;
    classifying the fluid voxels as intraretinal fluid (IRF), provided the fluid voxel locations are above the separating retina layer boundary; and
    classifying the fluid voxels as subretinal fluid (SRF), provided the voxel locations are below the separating retina layer boundary.

17. The method of claim 16, wherein the separating retina layer boundary is a junction of inner and outer photoreceptor segments of the retina.

18. The method of claim 1, wherein the first retina layer boundary is the inner limiting membrane.

19. The method of claim 18, wherein the second retina layer boundary is Bruch's membrane.

20. A system for quantifying retinal fluid volume in an optical coherence tomography (OCT) dataset, comprising:
    an OCT system configured to acquire a structural OCT dataset for a sample, wherein the structural OCT dataset is comprised of B-scan images and C-scan images;
    a logic subsystem; and
    a data holding subsystem comprising machine-readable instructions stored thereon that are executable by the logic subsystem to:
       delineate a first retina layer boundary from the structural OCT dataset;
       delineate a second retina layer boundary from the structural OCT dataset;

segment the B-scan images and the C-scan images in a region between the first retina layer boundary and the second retina layer boundary to obtain a 3D retinal fluid segmentation; and calculate a volume of fluid enclosed by the 3D retinal fluid segmentation.

21. The system of claim 20, wherein the instructions are further executable by the logic subsystem to flatten, prior to segmenting the B-scan images and the C-scan images, the structural OCT dataset using the first retina layer boundary as a reference plane, thereby generating a flattened structural OCT dataset, wherein, to segment the B-scan images and the C-scan images, the logic subsystem is to segment the B-scan images and the C-scan images of the flattened structural OCT dataset.

22. The system of claim 21, wherein, to segment the B-scan images and the C-scan images, the logic subsystem is to:

segment the B-scan images of the flattened structural OCT dataset in an x-direction, the segmenting limited to the region between the first retina layer boundary and second retina layer boundary, thereby generating an x-direction segmentation;

segment the B-scan images of the flattened structural OCT dataset in a y-direction, the segmenting limited to the region between the first retina layer boundary and second retina layer boundary, thereby generating an y-direction segmentation;

segment the C-scan images of the flattened structural OCT dataset in the z-direction, wherein the segmenting is limited to the region between the first retina layer boundary and second retina layer boundary, thereby generating a z-direction segmentation; and combine the x-direction segmentation, y-direction segmentation, and z-direction segmentation, thereby generating the 3D retinal fluid segmentation.

23. The system of claim 22, wherein, to segment the B-scan or C-scan images, the logic subsystem is to:

select a B-scan or C-scan image from the structural OCT dataset;

calculate a clustering probability map for the B-scan or C-scan image;

calculate a set of parameter values based on the clustering probability map;

initialize a level set algorithm with the set of parameter values;

apply the level set algorithm to the B-scan or C-scan image; and return a segmented B-scan or C-scan image, wherein the boundaries of fluid-filled regions of the retina are delineated in the segmented B-scan or C-scan image.

24. The system of claim 20, wherein the instructions are further executable by the logic subsystem to remove segmentation artifacts from the 3D retinal fluid segmentation prior to calculating the volume of fluid enclosed by the 3D retinal fluid segmentation.

25. The system of claim 24, wherein, to remove segmentation artifacts from the 3D retinal fluid segmentation, the logic subsystem is to:

select a segmented B-scan image;

select a segmentation contour within the segmented B-scan image;

apply a Gaussian filter to the segmentation contour, thereby generating a smoothed contour;

calculate a curvature equation for the smoothed contour according to:

$$\tau(l, \sigma_1) = \frac{X'(l, \sigma_1)Y''(l, \sigma_1) - Y'(l, \sigma_1)X''(l, \sigma_1)}{\{[X'(l, \sigma_1)]^2 + [Y'(l, \sigma_1)]^2\}^{3/2}} \quad (5)$$

where, $X(l, \sigma_1)$ and $Y(l, \sigma_1)$ are smoothed curves using Gaussian filter $g(l, \sigma_1)$, $X'(\bullet)$ and $X''(\bullet)$ are first and second derivatives of length l, respectively, $Y'(\bullet)$ and $Y''(\bullet)$ are first and second derivatives of length l, respectively, and a zero-crossing of $\tau(l,\sigma_1)$ indicates a curvature inflexion;

find a first number of inflection points along the curvature equation; and remove the segmentation contour, provided that the first number of inflection points exceeds a threshold value.

26. The system of claim 20, wherein the instructions are further executable by the logic subsystem to:

smooth the 3D retinal fluid segmentation, thereby generating a smoothed 3D retinal fluid segmentation;

select a segmented volume within the smoothed 3D retinal fluid segmentation; and remove the segmented volume, provided that the size of the segmented volume along each axis is less than a size threshold value.

27. The system of claim 20, wherein the instructions are further executable by the logic subsystem to:

obtain an OCT angiography dataset, wherein the OCT angiography dataset is computed from the structural OCT dataset and comprised of voxels having a specified voxel dimension;

classify voxels in the 3D retinal fluid segmentation that are located inside a segmentation contour as fluid, thereby generating a set of fluid voxels;

count the fluid voxels along each axial position in the 3D retinal fluid segmentation, provided that the voxels are located between the first retina layer boundary and second retina layer boundary, thereby generating a set of fluid thickness counts;

multiply the fluid thickness counts by a voxel dimension, thereby generating a set of fluid thickness values; and generate a 2D fluid thickness map from the set of fluid thickness values.

28. The system of claim 20, wherein the first retina layer boundary is the inner limiting membrane and the second retina layer boundary is Bruch's membrane.

* * * * *